(12) United States Patent
Mondelli

(10) Patent No.: US 10,167,333 B2
(45) Date of Patent: Jan. 1, 2019

(54) NEUTRALIZING HUMAN MONOCLONAL ANTIBODIES AGAINST HEPATITIS B VIRUS SURFACE ANTIGEN

(71) Applicant: Mario Umberto Francesco Mondelli, Milan (IT)

(72) Inventor: Mario Umberto Francesco Mondelli, Milan (IT)

( * ) Notice: Subject to any disclaimer, the term of this patent is extended or adjusted under 35 U.S.C. 154(b) by 171 days.

(21) Appl. No.: 15/111,571

(22) PCT Filed: Jan. 15, 2015

(86) PCT No.: PCT/EP2015/050717
§ 371 (c)(1),
(2) Date: Jul. 14, 2016

(87) PCT Pub. No.: WO2015/107126
PCT Pub. Date: Jul. 23, 2015

(65) Prior Publication Data
US 2016/0326233 A1 Nov. 10, 2016

(30) Foreign Application Priority Data

Jan. 16, 2014 (EP) .................................... 14151437

(51) Int. Cl.
*A61K 39/42* (2006.01)
*C07K 16/08* (2006.01)
*C07K 16/10* (2006.01)

(52) U.S. Cl.
CPC ............ *C07K 16/082* (2013.01); *C07K 16/10* (2013.01); *C07K 2317/21* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 7,585,500 B2 * | 9/2009 | Foltz | ............... | C07K 16/244 424/130.1 |
| 7,608,693 B2 * | 10/2009 | Martin | ............... | C07K 16/2866 530/387.9 |
| 7,846,435 B1 * | 12/2010 | Matsumoto | ........ | C07K 16/1232 424/133.1 |

FOREIGN PATENT DOCUMENTS

| | | |
|---|---|---|
| WO | 2009/069917 A1 | 6/2009 |
| WO | 2011/045079 A1 | 4/2011 |

(Continued)

OTHER PUBLICATIONS

NCBI BLAST Search Results with Matsumoto et al. (Year: 2018).*

(Continued)

*Primary Examiner* — Janet L Andres
*Assistant Examiner* — M Franco G Salvoza
(74) *Attorney, Agent, or Firm* — FisherBroyles LLP

(57) ABSTRACT

The invention is in the field of medical treatment and prevention. The invention provides an antibody or a part thereof capable of specifically binding to the Hepatitis B surface antigen (HBsAg) and having Hepatitis B Virus (HBV) neutralizing activity, wherein said antibody or fragment thereof comprises a light chain CDR1 region comprising the amino acid sequence of SEQ ID NO: 5, a light chain CDR2 region comprising the amino acid sequence of SEQ ID NO: 6, a light chain CDR3 region comprising the amino acid sequence of SEQ ID NO: 7, a heavy chain CDR1 region comprising the amino acid sequence of SEQ ID NO: 8, a heavy chain CDR2 region comprising the amino acid sequence of SEQ ID NO: 9 and a heavy chain CDR3 region comprising the amino acid sequence of SEQ ID NO: 10.

13 Claims, 4 Drawing Sheets

Figure 1:
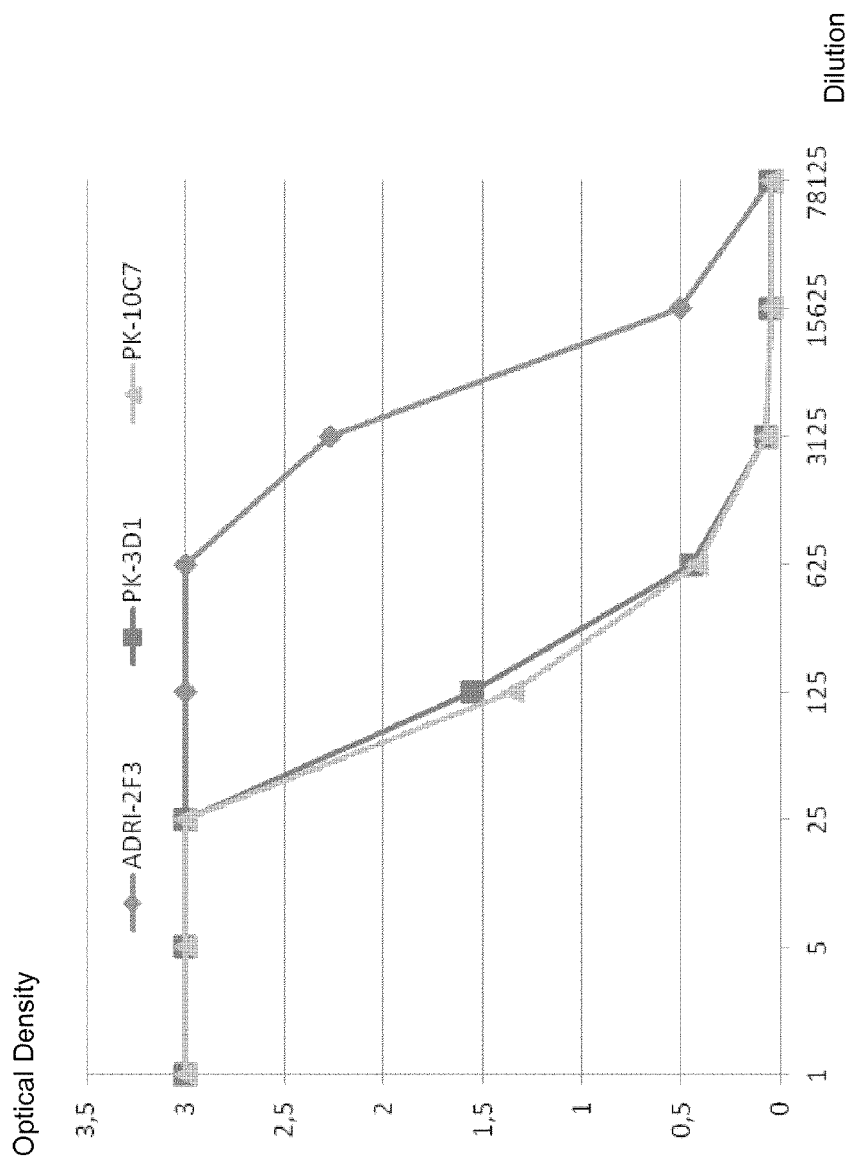

Specification includes a Sequence Listing.

(56) References Cited

FOREIGN PATENT DOCUMENTS

| WO | 2011/078456 A1 | 6/2011 | |
|---|---|---|---|
| WO | WO-2013165972 A2 * | 11/2013 | ............ C07K 16/082 |

OTHER PUBLICATIONS

NCBI BLAST Search Results with Foltz et al. (Year: 2018).*
Heavy Chain/SEQ ID No. 238 of U.S. Pat. No. 7,608,693 (Martin et al.), NCBI Blast Search Results (Year: 2018).*
Light Chain/SEQ ID No. 240 of U.S. Pat. No. 7,608,693 (Martin et al.), NCBI Blast Results (Year: 2018).*
Beck, J., et al., "Hepatitis B Virus replication", 2007, World Journal of Gastroenterology, 13(1): 48-64.
Cerino, A., et al., "A Human Monoclonal Antibody against Hepatitis B Surface Antigen with Potent Neutralizing Activity", 2015, PLOS One, vol. 10 (4): E0125704, 10 pages.
Eren, R., et al., "Preclinical Evaluation of Two Human Anti-Hepatitis B Virus (HBV) Monoclonal Antibodies in the HBV-Trimera Mouse Model and in HBV Chronic Carrier Chimpanzees", 2000, Hepatology, vol. 32(3): 588-596.
Glebe, D., et al., "Pre-S1 Antigen-Dependent Infection of Tupaia Hepatocyte Cultures with Human Hepatitis B Virus", 2003, Journal of Virology, vol. 77(17): 9511-9521.
International Search Report and Written Opinion dated Mar. 13, 2015 issued in PCT Patent Application No. PCT/EP2015/050717.
Schmitz, U., et al., "Phage Display: A Molecular Tool for the Generation of Antibodies", 2000, Placenta, 21, Supplement A, Trophoblast Research, 14, S.106-S112.
Shin, Y., et al., "Human monoclonal antibody against Hepatitis B virus surface antigen (HBsAg)", 2007, Antiviral Research, 75: 113-120.
Tajiri, K., et al. "Analysis of the epitope and neutralizing capacity of human monoclonal antibodies induced by hepatitis B Vaccine", 2010, Antiviral Research, 87: 40-49.

* cited by examiner

NEUTRALIZING HUMAN MONOCLONAL ANTIBODIES AGAINST HEPATITIS B VIRUS SURFACE ANTIGEN

CROSS-REFERENCE TO RELATED APPLICATIONS

This patent application is a 35 U.S.C. § 371 National Phase Application of International Patent Application No. PCT/EP 2015/050717, filed Jan. 15, 2015, and incorporated herein by reference in its entirety, which claims priority to European Application No. 14151437.2, filed Jan. 16, 2014, which is incorporated herein in its entirety.

REFERENCE TO SEQUENCE LISTING SUBMITTED ELECTRONICALLY

The content of the electronically submitted sequence listing in ASCII text file (Name 57912-157406SL.txt; Size: 4492 bytes; and Date of Creation: Jul. 14, 2016) filed with the application is incorporated herein by reference in its entirety.

FIELD OF THE INVENTION

The invention is in the field of medical treatment and prevention. The invention provides a monoclonal antibody that is capable of neutralizing hepatitis B infection and preventing, treating or ameliorating HBV associated diseases.

BACKGROUND OF THE INVENTION

Hepatitis B virus (HBV) is one of the world's most common infectious agents causing millions of infections each year [1]. Between 500,000 and 700,000 people die each year from chronic infection-related cirrhosis, hepatocellular carcinoma (HCC) or from fulminant hepatitis B [1,2]. Transmission occurs via percutaneous and mucosal exposure to infectious body fluids. Therefore, the most common route of transmission is sexual transmission. However, infection through blood transfusions and blood products has not been completely eliminated and contaminated injections during medical procedures, sharing of needles, syringes and paraphernalia among intravenous drug users still represent a major public health problem. Vertical transmission is common, especially in Asia and developing countries which have not implemented hepatitis B vaccination. Further, HBV poses a risk to healthcare workers exposed to accidental needle-stick injuries.

Hepatitis B vaccine is a vaccine developed for the prevention of hepatitis B virus infection. The vaccine contains one of the viral envelope proteins, hepatitis B surface antigen (HBsAg). It may be recombinantly produced in yeast cells, into which the genetic code for HBsAg has been inserted. Vaccination with Hepatitis B surface antigen (HBsAg) provides protection against HBV infection and prevents complications including liver cirrhosis and HCC. The control and the eventual elimination of HBV infection are possible with the appropriate use of hepatitis B vaccines, and this will reduce significantly the disease burden and its associated costs.

Although prevention of HBV infection may be effectively achieved by vaccination there are certain situations that require a different prophylactic approach. Liver transplantation for end-stage HBV-related liver disease is one such example. Hepatitis B immune globulin (HBIG) has played a central role in prophylaxis against recurrent hepatitis B in patients undergoing liver transplantation.

Prior to the routine use of HBIG as immunoprophylaxis, recurrence of HBV in the liver allograft occurred in up to 80%, and infrequently was associated with an aggressive fibrosing cholestatic variant that caused progressive graft dysfunction and significant mortality. The subsequent availability of safe and effective antiviral drugs led to additional survival benefits by improving prophylactic efficacy and preventing disease progression in those with recurrence [3].

HBIG is a polyclonal antibody to HBV surface antigen (HBsAg) derived from pooled human plasma. Although its mechanism of action is not yet completely understood, it is thought that HBIG acts in the circulation by preventing hepatocyte infection, binding to and neutralizing circulating virions expressing HBsAg and perhaps inducing lysis of infected cells [4]. Within the liver, HBIG may also prevent cell-to-cell infection as well as reduce HBsAg and virion secretion upon endocytosis into hepatocytes [5].

To provide maximal protection against re-infection of the liver graft, HBIG should be given frequently (typically daily) for the week following transplantation. The pivotal multicenter European trial demonstrated that long term administration of intravenous (IV) HBIG reduced hepatitis B recurrence rates from 75% to 36% and was associated with improved graft and patient survival [6]. Subsequent trials, using variable schedules for HBIG administration, confirmed the efficacy of HBIG as a monotherapy against recurrent HBV infection [7].

HBIG prophylaxis is expensive. HBIG are commonly administered intravenously at high dose, daily for the first week and monthly thereafter, which makes the current costs of management of patients transplanted for HBV-related cirrhosis prohibitive, even for developed countries. Dose reduction has been proposed for cost reduction, either based on a flat dose or on a response-guided basis in order to maintain circulating anti-HBs at a protective level. However, HBIG doses are variable and should be individualized among patients. It has also been proposed to abandon HBIG prophylaxis in favor of using antiviral drugs alone, however this is a very controversial issue [3].

The cost of HBIG treatment and prevention are not the only limitations to its use. Additional limitations include the following: i) supply is limited and depend on vaccinated human donors exhibiting high titer protective anti-HBs, ii) purification is time consuming and must undergo lengthy virus-inactivation procedures; iii) anti-HBs titer is variable and effective virus neutralization efficiency largely unknown being exclusively based on arbitrarily protective anti-HBs serum titers; iv) polyclonal immunoglobulin include several antibody specificities and may select for HBV mutants resistant to currently available antiviral drugs; v) HBIG preparations are currently combined with antiviral drugs to insure complete protection, thus adding to the costs.

In conclusion, there is an unmet medical need for a sustainable reagent allowing standardization of immunoprophylaxis of HBV re-infection in the liver transplant. Such a standardized reagent could then also beneficially be used in other settings, such as in the acute treatment of accidental needle-sticks and in the prevention of vertical, perinatal HBV transmission. Administration of anti-HBs antibodies is usually performed as a prophylactic measure while waiting for the full development of vaccine-induced adaptive immunity to HBV.

Monoclonal antibodies have been proposed and developed in order to address that need. Most monoclonal antibodies against HBV are of murine origin. Such murine antibodies have the inherent disadvantage that they evoke an immune reaction in a human recipient when used in a therapeutic or prophylactic composition.

Human monoclonal antibodies capable of neutralizing HBV infection have also been described.

WO 2011/045079 describes the isolation and characterization of 2D028, a monoclonal antibody specific for the large pre-S1 HBV envelope protein. The antibody reacts with an epitope slightly downstream of the N-terminus of pre-S1 (amino acids 21-47). It is stated at paragraph [00105] of WO 2011/045079 that HBV infection was essentially undetectable at 10 micrograms per milliliter of the antibody.

Another set of monoclonal antibodies termed HBV-17 and HBV-19 were described in Eren et al., Hepatology 32 (2000), 588-596. These antibodies had a specific activity of 514 IU/mg and 2,900 IU/mg respectively, as described on page 590, bottom of left column of Eren et al., Hepatology 32 (2000), 588-596.

Figure 4:
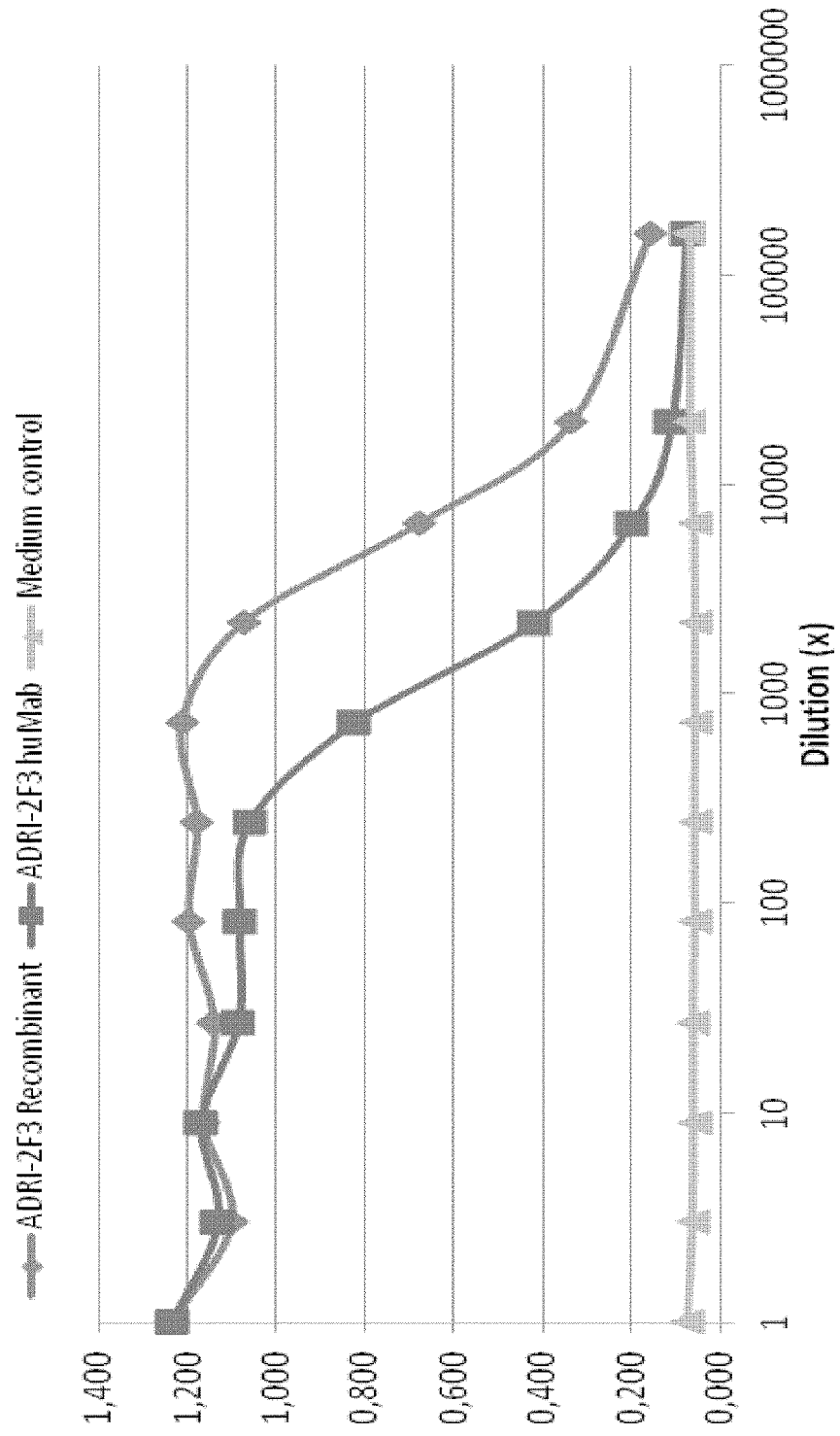

Yet another series of human monoclonal antibodies has been described in Tajiri et al., Antiviral Research 87 (2010) 40-49. These antibodies did not seem to provide full protection against HBV infection, even not at the highest concentrations tested. FIG. 4 in Tajiri et al., Antiviral Research 87 (2010) 40-49 shows that there is still residual activity after neutralization of HBV with each of the antibodies tested.

Human monoclonal antibody HB-C7A has been described in Shin et al., Antiviral Research 75 (2007); 113-120. This antibody was capable of fully preventing HBV infection in two chimpanzees after mixing 100 CID50 of HBV and 100 microgram of HB-C7A. The antibody is said to have a titer of 2600 units per mg of antibody.

Despite of this progress in the art, there is a desire for more potent human monoclonal antibodies in order to cure or prevent HBV infection in humans more efficiently and effectively.

SUMMARY OF THE INVENTION

It is the object of the present invention to provide a monoclonal antibody with a potent HBsAg neutralizing activity and/or a higher titer as the prior art antibodies.

This goal is achieved by providing a human monoclonal antibody ADRI-2F3 specifically reactive with Hepatitis B surface antigen (HBsAg). This monoclonal antibody comprises a human heavy chain and a light chain, each comprising a variable and a constant region. The variable regions of the heavy and light chains each comprise 3 complementarity determining regions (CDRs) which together constitute the specific binding site for the HBsAg antigen.

The invention relates to the monoclonal antibody and its uses. In one aspect, the invention therefore relates to an antibody specifically binding Hepatitis B surface antigen (HBsAg) comprising at least 6 complementarity determining regions (CDR) with an amino acid sequence according to SEQ ID NO: 5, SEQ ID NO: 6, SEQ ID NO: 7, SEQ ID NO: 8, SEQ ID NO: 9 and SEQ ID NO: 10.

The invention also relates to the first and second medical use of the antibody, in particular in the treatment, prevention or prophylaxis of hepatitis B infection The invention also provides a nucleic acid encoding the variable heavy and light chains of the antibody according to the invention. These nucleic acids may advantageously be used in the production of recombinant antibodies with the same, comparable, or improved binding characteristics as the human monoclonal antibody ADRI-2F3.

DETAILED DESCRIPTION OF THE INVENTION

Three human B-cell clones were generated from PBMC of one patient (PK) convalescing from acute hepatitis B and one vaccinated healthy donor (ADR). The clones designated PK-3D1 and PK-1007 secreted IgG1κ and displayed low titer binding to HBsAg and no or limited neutralizing activity. These clones were found to recognize a linear epitope as evidenced by their reactivity with HBsAg antigen on a Western blot with the 24 kD major S viral envelope protein.

Surprisingly, one clone, obtained from the vaccinated healthy donor ADR recognized a conformational epitope, as evidenced by the absence of reactivity on Western blot.

This clone, designated ADRI-2F3, secreted IgG1λ (IgG1 lambda) and showed high titer binding to HBsAg in a HBsAg ELISA. Much to our surprise, the antibody exhibited a very potent neutralizing activity. It was found that less than 2.7 nanograms of the antibody was capable of neutralizing 100 million ($10^8$) HBV particles.

Human mAb ADRI-2F3 recognized a conformational epitope on HBsAg, and that it is likely that the epitope resides in the first extracellular loop domain of the major S protein (otherwise named the common "a" determinant) as over 70% of the circulating antibodies in vaccinated persons do.

The neutralizing capacity of ADRI-2F3 was found to be very high. Whereas the antibodies in the prior art (WO 2011/045079) were effective in neutralizing HBV at concentrations between 18 and 88 nanograms per milliliter (WO 2011/045079, page 37, table 2) the monoclonal antibody according to the invention was capable of neutralizing HBV efficiently at 2.7 nanograms per milliliter.

The extreme potency of the ADRI-2F3 antibody according to the invention was further corroborated by determining its protective titer in a standard anti-HBs titration kit (Abbott Architect anti-HBs). It was found therein that mAb ADRI-2F3 had a protective titer of over 43,000 IU/mg of antibody. In comparison, prior art antibodies HBV-17 and HBV-19 (Eren et al., Hepatology 32 (2000), 588-596) had titers of 514 IU/mg and 2,900 IU/mg of antibody in this same assay. Prior art antibody HB-C7A had a protective titer of 2600 IU/mg of antibody in this assay (Antivir. Res. (2007) 75: 113-120 and Antivir. Res. (2008) 79: 188-191) In comparison, the conventional protective titer of anti-HBs in vaccinated persons is arbitrarily set at 10-12 IU/ml [18].

Protective titers of HBV antibodies are expressed in International Units (IU) which allows standardization over different assays. In 1977, an International Reference Preparation for anti-HBs immunoglobulin (W1042) was established. The plasma used in the preparation of this standard was derived from individuals who had been naturally infected with hepatitis B virus [15, 16].

Because only 250 vials were prepared from the original plasma, a Second WHO International Standard for anti-hepatitis B surface antigen was subsequently prepared from a bulk of 5% (w/v) protein concentration hepatitis B immunoglobulin which had been formulated to a target concentration of 100 IU/ml according to the 1st IS reference preparation [17].

Human antibody ADRI-2F3 was characterised by determining the nucleotide sequence of its variable regions (table 1) and the complementarity determining regions (CDR)

therein (table 2). It was thus established that the invention relates to an antibody or part thereof specifically binding Hepatitis B surface antigen (HBsAg) comprising at least 6 complementarity determining regions (CDR) with an amino acid sequence according to SEQ ID NO: 5, SEQ ID NO: 6, SEQ ID NO: 7, SEQ ID NO: 8, SEQ ID NO: 9 and SEQ ID NO: 10.

In other words, the invention relates to an antibody or part thereof capable of specifically binding to the Hepatitis B surface antigen (HBsAg) and having Hepatitis B Virus (HBV) neutralizing activity, wherein said antibody or fragment thereof comprises a light chain CDR1 region comprising the amino acid sequence of SEQ ID NO: 5, a light chain CDR2 region comprising the amino acid sequence of SEQ ID NO: 6, a light chain CDR3 region comprising the amino acid sequence of SEQ ID NO: 7, a heavy chain CDR1 region comprising the amino acid sequence of SEQ ID NO: 8, a heavy chain CDR2 region comprising the amino acid sequence of SEQ ID NO: 9 and a heavy chain CDR3 region comprising the amino acid sequence of SEQ ID NO: 10.

As used herein, the term "antibody" refers to single chain antibodies, fragment antigen binding regions, recombinantly produced antibodies, monoclonal antibodies, single domain antibodies, and the like.

The term "or part thereof" or "or fragment thereof" in the context of an antibody or other specific binding molecule is meant to refer to the part of the antibody or specific binding molecule that makes up the specific binding site of the antibody or specific binding molecule and may be interpreted as the part of an antibody or specific binding molecule that is still capable to react with the same epitope as the entire antibody or specific binding molecule.

The term "specifically binding Hepatitis B surface antigen (HBsAg)" is used herein to indicate that the antibody should be reactive with HBsAg and not or only to a limited extent with an unrelated antigen. The term HBsAg is known in the art and refers to a surface protein of HBV. HBsAg is encoded by a Gene S, which consists of one long open reading frame but contains three in frame "start" (ATG) codons that divide the gene into three sections, pre-S1, pre-S2, and S. Because of the multiple start codons, polypeptides of three different sizes called large, middle, and small (pre-S1+pre-S2+S, pre-S2+S, or S) are produced (Beck et al., World J. Gastroenterol. (2007) 13; 48-64. Because the donor from which the antibody was derived was a vaccinated individual and the currently commercially available vaccines are made of S protein only it may be inferred that the specificity was exclusively for the S protein, not pre-S1 or pre-S2.

As used herein, the term "Complementarity determining regions (CDRs)" refers to regions within antibodies (also known as immunoglobulins), B-cell receptors and T-cell receptors where these proteins complement an antigen's shape.

Thus, CDRs determine the protein's avidity (roughly, bonding strength) and specificity for specific antigens. The CDRs are the most variable part of the molecule, and contribute to the diversity of these molecules, allowing the antibody and the T-cell receptor to recognize a vast repertoire of antigens In the amino acid sequence of a variable domain of an antigen receptor there are three CDRs (CDR1, CDR2 and CDR3), arranged non-consecutively. Since the antigen receptors are typically composed of two variable domains (on two different polypeptide chains, heavy and light chain), there are six CDRs for each antigen receptor that can collectively come into contact with the antigen. A single antibody molecule has two mostly identical antigen receptors and therefore contains two pairs of six CDRs, in total twelve CDRs. Sixty CDRs can be found on a pentameric IgM molecule.

Within the variable domain, CDR1 and CDR2 are found in the variable (V) region of a polypeptide chain, and CDR3 includes some of V, all of diversity (D, heavy chains only) and joining (J) regions. CDR3 is the most variable.

Since most sequence variation associated with immunoglobulins and T cell receptors are found in the CDRs, these regions are sometimes also referred to as hypervariable regions. Among these, CDR3 shows the greatest variability as it is encoded by a recombination of the VJ in the case of a light chain region and VDJ in the case of heavy chain regions.

In a preferred embodiment, the invention relates to an antibody that comprises the entire heavy and light chain variable regions of antibody ADRI-2F3. The invention thus also relates to an antibody as described above comprising the amino acid sequence according to SEQ ID NO: 2 and SEQ ID NO: 4. In a further preferred embodiment, the antibody is a fully human antibody.

In an alternative embodiment, the antibody may be a recombinant antibody.

The production of recombinant monoclonal antibodies is well known in the art and involves technologies, referred to as repertoire cloning or phage display/yeast display. Recombinant antibody engineering involves the use of viruses or yeast to create antibodies, rather than mice. These techniques rely on rapid cloning of immunoglobulin gene segments to create libraries of antibodies with slightly different amino acid sequences from which antibodies with desired specificities can be selected (Siegel et al., Transfusion clinique et biologique: (2002) Journal de la Société française de transfusion sanguine 9:15-22.

The phage antibody libraries are a variant of the phage antigen libraries first invented by George Pieczenik (Pieczenik, MRC Laboratory of Molecular Biology (LMB). 2009) These techniques can be used to enhance the specificity with which antibodies recognize antigens, their stability in various environmental conditions, their therapeutic efficacy, and their detectability in diagnostic applications (Schmitz et al., (2000). "Phage display: a molecular tool for the generation of antibodies—a review". Placenta 21 (Suppl A): S106-S112). Fermentation chambers have been used to produce these antibodies on a large scale The antibodies as presented herein may advantageously be used to treat, prevent or ameliorate an infection with HBV or a disease caused thereby. In one aspect, the invention relates thus to an antibody as described above for use as a medicament, more in particular for use in the treatment or prevention of hepatitis B infection. The antibody according to the invention is particularly suited for that purpose since it neutralizes hepatitis B virus very efficiently and effectively.

As used herein, the term "prevention" renders a process impossible by an advanced provision. Prophylaxis is the process of guarding against the development of a specific disease by an action or treatment that affects pathogenesis.

Due to its extreme potency, the antibody may be administered at very low quantities, thus contributing to a cost-effective treatment. In general, the antibody may preferably be administered to a mammal in order to maintain a serum level of between 12 and 5000 IU per ml serum. The minimum level is preferably 12 IU per ml since the conventional protective titer of anti-HBs in vaccinated persons is arbitrarily set at 12 IU/ml. In some cases, the minimum level may be higher, such as 15, 20, 25, 50, 100 or even 200

IU per milliliter serum or above. There is no upper limit for the level of antibodies, however, for practical purposes an upper level may be set at 5000 IU/ml serum. Levels of between 100 and 500 IU, more preferably between 150 and 300 IU such as about 200 IU are arbitrarily defined as desirable to avoid reinfection of the liver graft. An upper limit may also be expressed as 10 mg of antibody per kg body weight of the vaccinated subject per dose.

In another words, the invention relates to a method for preventing or treating HBV infection or a disease caused thereby in a mammal, comprising the step of administering to the mammal a human antibody comprising a heavy chain variable region consisting of an amino acid sequence according to SEQ ID NO: 2 and a light chain variable region consisting of an amino acid sequence according to SEQ ID NO: 4 in an effective amount.

The nucleic acids described herein may advantageously be used to produce further antibodies such as recombinant antibodies or other binding molecules effective in the treatment of HBV infection. They may also be used as research tools, for instance to create libraries for the research towards even more improved antibodies and binding reagents. The invention therefore also relates to a nucleic acid encoding a heavy chain variable region consisting of an amino acid sequence according to SEQ ID NO: 2 or a light chain variable region consisting of an amino acid sequence according to SEQ ID NO: 4, or its complement.

Nucleic acids encoding the CDRs of the antibodies described herein may be an equally good source of research materials. The invention therefore also relates to a nucleic acid encoding an amino acid sequence according to SEQ ID NO: 5, SEQ ID NO: 6, SEQ ID NO: 7, SEQ ID NO: 8, SEQ ID NO: 9 and SEQ ID NO: 10.

A further preferred nucleic acid comprises a nucleotide sequence according to SEQ ID NO: 1 or SEQ ID NO: 3.

LEGEND TO THE FIGURES

FIG. 1: Titration curve of monoclonal antibody binding to HBsAg in an ELISA. Diamonds: ADRI-2F3, Squares: PK-3D1, Triangles PK-1007.

Figure 2:
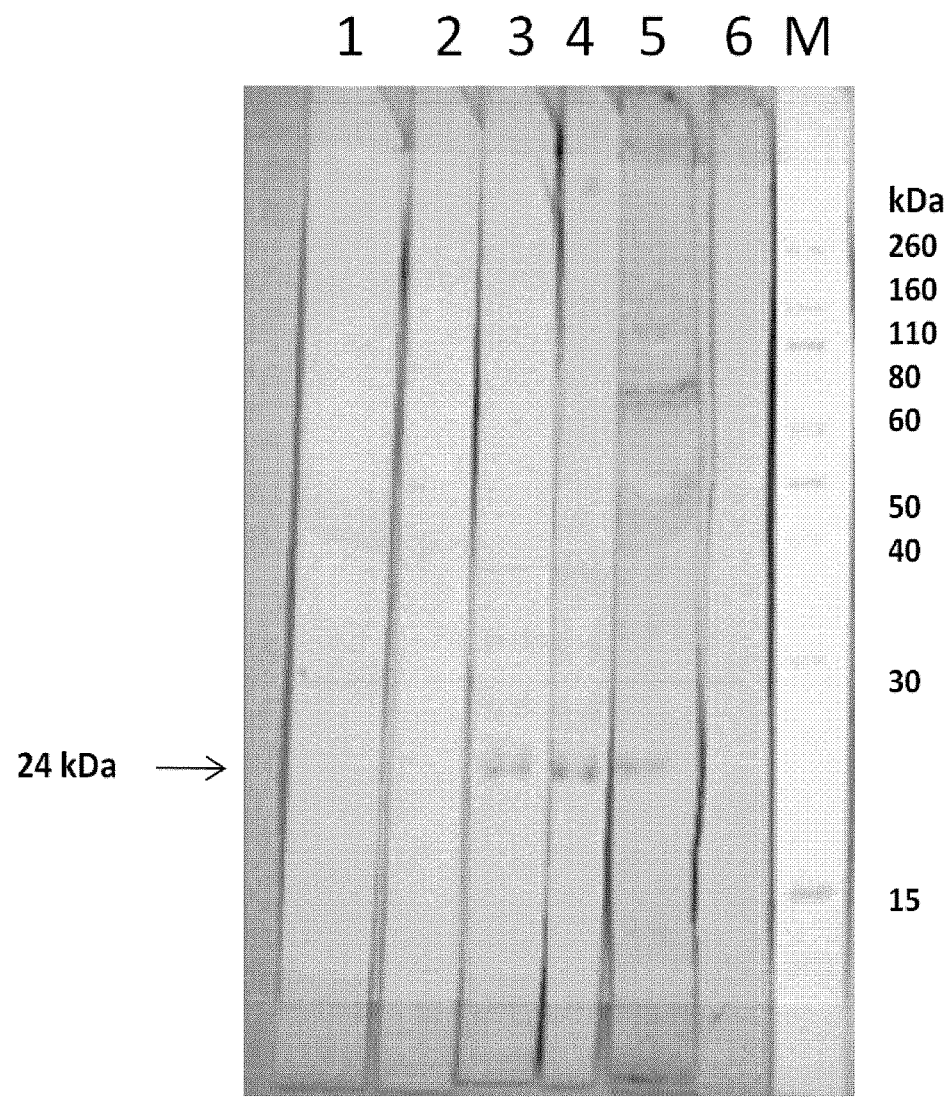

FIG. 2: Western blot showing reactivity of antibodies ADRI-2F3 (lanes 1 and 2), PK-1007 (lane 3) and PK-3D1 (lane 4). Lane 5; positive control serum, lane 6; negative control. MW indicates a molecular weight marker. Note that in lanes 3, 4 and 5 a 24 kDa band is recognized, indicating binding to the HBsAg polypeptide.

Figure 3:
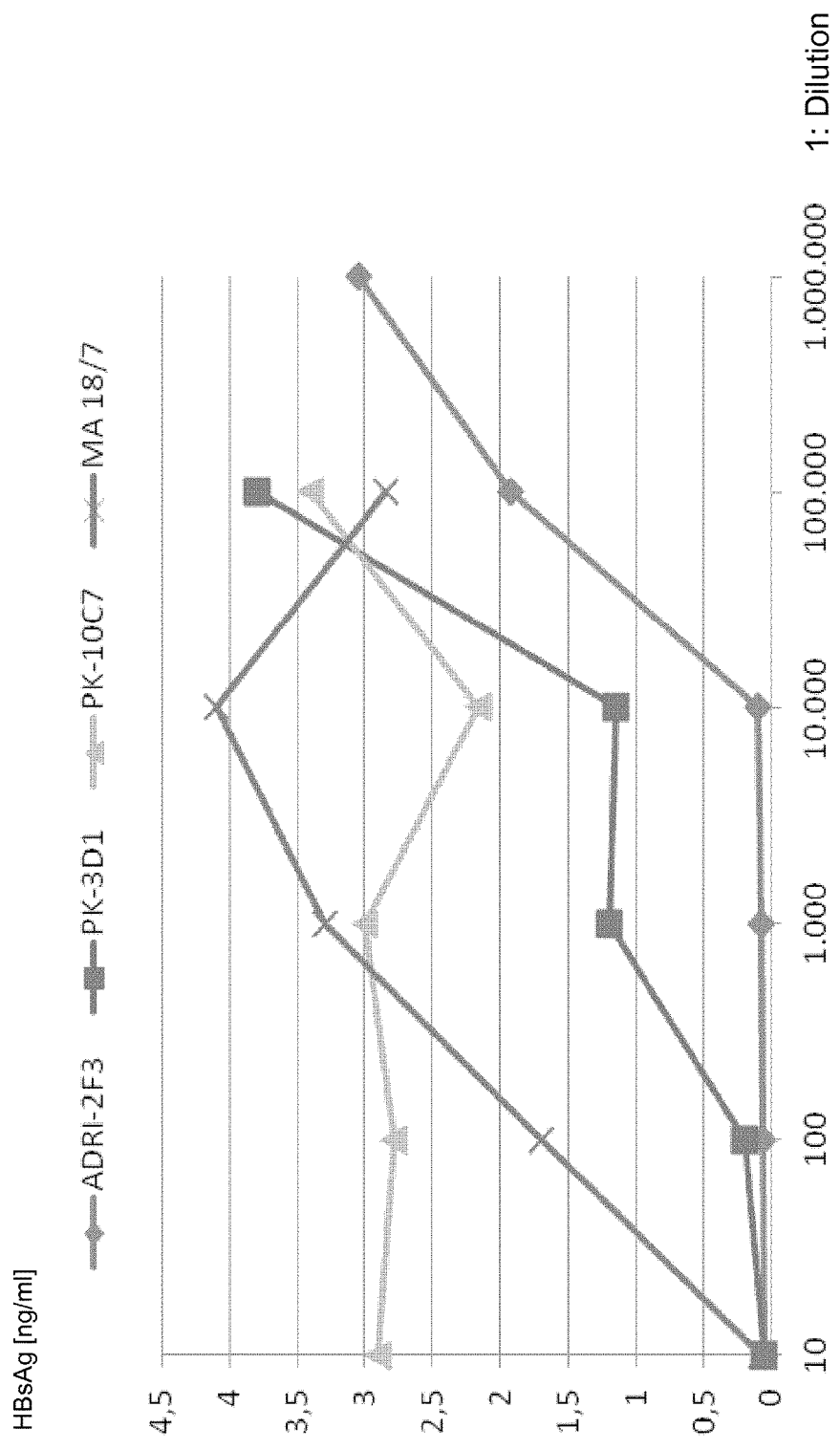

FIG. 3: Neutralizing activity of three human monoclonal antibodies PK-3D1, PK-1007 and ADRI-2F3 in comparison with mouse monoclonal antibody MA18/7. It is shown herein that a dilution of 1:10.000 of monoclonal antibody supernatant ADRI-2F3 completely neutralizes the activity of HBV, whereas EC50 is reached at a dilution of 1:100.000.

FIG. 4: reactivity of recombinant antibody ADRI-2F3 versus human monoclonal ADRI-2F3. The titration curve shows that the recombinant antibody is about 10 times as reactive as the original human monoclonal antibody.

EXAMPLES

Example 1

Isolation of HBsAg Specific B-cell Clones

Peripheral blood mononuclear cells (PBMC) were obtained from a vaccinated healthy donor (ADR) and from a person convalescing from acute hepatitis B (PK). Both subjects showed high serum anti-HBsAg titers. PBMC were isolated by standard density gradient centrifugation and B cells negatively purified using a B cell isolation kit (B cell isolation kit II, code no 130-042-201 MACS—Miltenyi Biotec). B cells ($10^6$/ml, purity >95%) were then incubated with undiluted supernatant from the EBV-productive B95-8 marmoset cell line for 24 h at 37 degrees Celsius, washed and incubated in complete media consisting of RPMI-1640 supplemented with 10% fetal bovine serum (code SH30071.03 HyClone), 2.5 µg/ml CpG-2006 (Microsynt) and 10 ng/ml IL-2 (code no 202-IL R&D Systems) as described [8], with the modification that enrichment of CD27+ memory B cells was omitted. Approximately $3 \times 10^3$ B cells in complete media were then seeded in each well of a 96-well round-bottom plate in the presence of irradiated feeder cells and incubated for 5 days after which IL-6 was added to a final concentration of 20 ng/ml. After evident visual outgrowth of lymphoblastoid cells, supernatants were tested by ELISA for the presence of anti-HBV envelope antibodies using a recombinant HBsAg preparation. Cultures exhibiting a 492 nm optical density >1 were cloned and subcloned by limiting dilution in complete media+IL-6 to obtain stable Ag-specific B-cell clones. A general procedure for cloning of B-cells by limiting dilution is found in references 9-12.

After evident visual outgrowth of lymphoblastoid cells, supernatants were tested by ELISA for the presence of anti-HBV envelope antibodies using a recombinant HBsAg preparation. Cultures exhibiting a 492 nm optical density >1 were cloned and subcloned by limiting dilution in complete media+20 ng/ml IL-6 in the presence of irradiated feeder cells to obtain stable Ag-specific B-cell clones.

Three human B-cell clones (ADRI-2F3, PK-10C7 and PK-3D1) were derived from the two subjects ADR and PK.

Example 2

Determining B-cell Clone Specificity

Specificity of the B-cell clones ADRI-2F3, PK-10C7 and PK-3D1 was determined by testing the supernatants by standard ELISA using a recombinant HBsAg preparation containing pre-S1, pre-S2 and S proteins. Monoclonal ADRI-2F3 secreted IgG1 lambda, whereas PK-10C7 and PK-3D1 secreted IgG1 kappa. All three mAbs showed strong binding to HBsAg in ELISA (FIG. 1). Binding of PK-10C7 and PK-3D1 was comparable, they showed clear binding at a dilution of 1/625. MAb ADRI-2F3 showed a clearly detectable binding to HBsAg at a dilution of 1/15625.

Binding to the common "a" determinant on the S polypeptide was determined by a competition ELISA using a murine mAb Hyb-824 (Cosmo Bio Co., LTD. Code no 2ZHB11 Cosmo Bio Co. LTD.) specific for the same region. Briefly, microtiter plates were coated with HBsAg at a concentration of 1 µg of 0.05M bicarbonate buffer (pH 9.6) per ml at 4° C. overnight. After saturation with 0.1 M PBS containing 2% bovine serum albumin (BSA). Murine monoclonal antibody Hyb-824 was diluted to a concentration of 200 ng/well and incubated at increasing concentrations (0 ng/w—400 ng/w) of human monoclonal antibodies ADRI-2F3, PK3D1 and PK10C7 for 1 h at 37° C. Plates were washed with PBS+0.05% Tween20, then 100 µl of diluted HRP-AffiniPure-goat anti-mouse IgG (H+L) (code 115-035-062 Jackson-ImmunoResearch) in 2% BSA-PBS were added and incubated for 1 h at 37° C. After washing again with PBS+0.05% Tween20, 100 µl of OPD solution (code S2045 DAKO) were added and the O.D. measured at 492 nm. Humab anti-HCV CM3-B6 and anti-HBV preS1 MA18/7 were used as negative control, whereas Hyb824 alone was used as positive control.

Western blot analysis using recombinant denatured HBsAg as antigen showed that PK-10C7 and PK-3D1 recognized a sequential, denaturation-insensitive epitope located within a band corresponding to the expected molecular weight (24 kDa) of the major S envelope protein [14], whereas ADRI-2F3 did not bind to any protein band, indicating that it recognized a denaturation-sensitive conformational epitope (FIG. 2).

Example 3

HBV Neutralization Assay and mAb Neutralizing Activity

A neutralization assay was performed as previously described [13]. Briefly, primary *Tupaia belangeri* hepatocyte cultures were inoculated with purified human serum HBV at a ratio of 100 HBV genome/hepatocyte. To determine whether the uptake of HBV by primary *Tupaia* hepatocytes could be prevented by human anti-HBs mAbs, HBV was preincubated with three different human mAbs ADRI-2F3, PK-10C7, PK-3D1, at dilutions ranging from 1:10 to 1:10^6.

The neutralization capability of the human anti-HBs mAbs was directly compared with the preS1-specific antibody MA18/7 which was previously shown to exhibit significant neutralizing activity in the *Tupaia* hepatocyte in vitro infection assay [13]. The read-out of successful HBV-infection of these cultures was newly produced HBsAg at a time point between 11 to 15 days after infection. Neutralization was considered effective if no viral protein production was detectable in the culture supernatant [13].

It was found that ADRI-2F3 supernatant showed strong and effective neutralization activity up to 1:10,000 dilution. Since the specific IgG1 concentration in the supernatant was 27 microgram per ml (ug/ml), it can be calculated that monoclonal antibody ADRI-2F3 efficiently neutralized HBV at concentrations of at least 2.7 nanograms/ml (ng/ml, FIG. 3).

Since the HB virion production by infected *Tupaia* hepatocytes was 10^8/ml it can also be derived that no more than 2.7 ng/ml were sufficient to neutralize 10^8 HBV particles.

PK mAb supernatant showed contrasting behaviors. Thus, PK-10C7 did not neutralize infection of *Tupaia* hepatocytes at all, whereas PK-3D1 showed neutralizing activity down to a dilution of 1:10^2 (about 200 ng/ml). This neutralizing activity still proved to be better than the standard murine MA18/7 anti-pre-S1 mAb used as positive neutralization standard (1:10, corresponding to a concentration of 100 μg/ml) (FIG. 3).

Example 4

Sequencing of mAb ADRI-2F3 Variable Domains

The sequence of the monoclonal antibody ADRI-2F3 was determined by 5' Rapid Amplification of cDNA Ends (RACE). Total RNA was extracted from viable B-cell clone cultures treated with Trizol-containing buffer. The coding sequences for the variable heavy and light domains were determined by standard procedures.

Sequencing (in sense and in antisense direction) of n=20 VH and n=20 VL cDNA clones of the 5' RACE reaction on RNA isolated from human B-cell clone ADRI-2F3 yielded clear sequences for both the VH and the VL domains (n=38 and 36 identical sequences, respectively).

Nucleic acid and amino acid sequences of variable light chains (VL) and variable heavy chains (VH) are shown in table 1.

TABLE 1

Amino acid sequences of variable heavy and light chains of antibody ADRI-2F3.

| Clone ADRI-2F3 | Nucleic acid sequence | SEQ ID NO: | Amino Acid sequence | SEQ ID NO: |
|---|---|---|---|---|
| Heavy chain | gaggtgcagg tgttggagtc tggggaggc ttggtacagc cggggggtc cctgagactc tcctgtgcag cctctggatt caggtttagc agctatgcca tgagttgggt ccgccaggct ccagggaagg ggctggagtg ggtctcaggt attagtggta ctggtgaaaa cacatactac gcagactccg tgaagggccg gttcaccatc tccagagaca attccaagaa cacgctgtac gtgcaaatga acagcctgag agccgaagac acggccgtat attactgtgc gaaagatgcg atcttgggca gtggccaccc ctggtacttc catgtctggg gccgtggcac cctggtcact gtctcctca | 1 | EVQVLESGGG LVQPGGSLRL SCAASGFRFS SYAMSWVRQA PGKGLEWVSG ISGTGENTYY ADSVKGRFTI SRDNSKNTLY VQMNSLRAED TAVYYCAKDA ILGSGHPWYF HVWGRGTLVT VSS | 2 |
| Light Chain | tcctatgtgc tgactcagcc tccctcggtg tcagtggccc caggacagac ggccaggatg acctgtgggg gaaacaacat tggaagtgaa agtgtgcact ggttccagca gaagccaggc caggcccctg tgctggtcgt ctatgatgat agcgaccggc cctcagggat ccctgagcga ttctctggct ccaactctgg gaacacggcc accctgacca tcagtagggt cgaagccggg gatgaggccg actattactg tcaggtgtgg gatagtagta gtgatcatgc tgtgttcgga ggaggcaccc agctgaccgt cctc | 3 | SYVLTQPPSV SVAPGQTARM TCGGNNIGSE SVHWFQQKPG QAPVLVVYDD SDRPSGIPER FSGSNSGNTA TLTISRVEAG DEADYYCQVW DSSSDHAVFG GGTQLTVL | 4 |

Germline alignment within the IMGT framework allowed identification of complementarity determining regions (CDRs) which determine the specificity for binding of the antibody to HBsAg. Details of the position and sequences of CDR1, CDR2 and CDR3 are provided in table 2.

TABLE 2 identification of CDRs of antibody ADRI-2F3

| CDR | Chain | Position in IMGT framework 1 | Amino Acid Sequence | SEQ ID NO: |
|---|---|---|---|---|
| CDR1 | Light | 27-38 | NIGSES | 5 |
| CDR2 | Light | 56-65 | DDS | 6 |
| CDR3 | Light | 105-117 | QVWDSSSDH | 7 |

TABLE 2-continued identification of CDRs of antibody ADRI-2F3

| CDR | Chain | Position in IMGT framework 1 | Amino Acid Sequence | SEQ ID NO: |
|---|---|---|---|---|
| CDR1 | Heavy | 27-38 | GFRFSSYAM | 8 |
| CDR2 | Heavy | 56-65 | ISGTGENT | 9 |
| CDR3 | Heavy | 105-117 | AKDAILGSGHPWYFHV | 10 |

Example 5

Cloning and Eukaryotic Production of Recombinant ADRI-2F3 hIgG1 Lambda

Variable heavy and light domain sequences obtained as described above, were cloned into eukaryotic expression vectors pMQR-hIgG1 and pMQR-hIg lambda (ModiQuest Research). Recombinant antibodies were produced in transiently transfected Hek293 cells (ModiQuest Research). Recombinant antibody derived from monoclonal antibody ADRI-2F3 was designated as ADRI-2F3-130925NS. Recombinant antibody ADRI-2F3-130925NS was verified to contain the heavy and light chains of the human monoclonal antibody ADRI-2F3.

Example 6

Reactivity of Recombinant Antibody

Reactivity of the recombinant antibodies towards HBsAg was determined in an ELISA, using a supernatant from the original B-cell clone ADRI-2F3 for comparison. To this end, HBsAg was coated in carbonate buffer in an ELISA plate at 4 C.°, o/n. Following blocking, serial dilutions of antibody preparations were allowed to bind at room temperature in duplicate. Plates were washed and bound Ab visualized using goat anti-human IgG-HRP and TMB (extinction was read at 450 nm).

Recombinant antibody ADRI-2F3-130925NS and human monoclonal antibody ADRI-2F3 were tested for reactivity towards HBsAg and complete medium was used as negative control.

Recombinant antibody ADRI-2F3-130925NS showed an identical specificity as the original monoclonal antibody ADRI-2F3. Recombinant ADRI-2F3-130925NS proved to be reactive towards HBsAg, whereas it was even found that recombinant ADRI-2F3-130925NS displayed a reactivity of approximately one log 10 scale above the reactivity of the originating human B-cell clone. This is shown in FIG. 4.

This experiment conclusively shows that a recombinant antibody with the same specificity may be produced from the human monoclonal antibody ADRI-2F3 wherein the recombinant antibody comprises the heavy and light variable chains of antibody ADRI-2F3. It was thereby shown that the human monoclonal antibody could be cloned, produced in vitro, and retain its activity towards its target antigen (HBsAg).

REFERENCES

1. Lavanchy D. Worldwide epidemiology of HBV infection, disease burden, and vaccine prevention. J Clin Virol 2005; 34:S1-S3.
2. World Health Organization. Available from <www.who.int>.
3. Fox A N, Terrault N A. The option of HBIG-free prophylaxis against recurrent HBV. J Hepatol 2012; 56:1189-1197.
4. Shouval D, Samuel D. Hepatitis B immune globulin to prevent hepatitis B virus graft reinfection following liver transplantation: a concise review. Hepatology 2000; 32:1189-1195.
5. Schilling R, Ijaz S, Davidoff M, et al. Endocytosis of hepatitis B immune globulin into hepatocytes inhibits the secretion of hepatitis B virus surface antigen and virions. J Virol 2003; 77:8882-8892.
6. Samuel D, Muller R, Alexander G, Fassati L, Ducot B, Benhamou J P, et al. Liver transplantation in European patients with the hepatitis B surface antigen. N Engl J Med 1993; 329:1842-1847.
7. Terrault N A, Zhou S, McCory R W, et al. Incidence and clinical consequences of surface and polymerase gene mutations in liver transplant recipients on hepatitis B immunoglobulin. Hepatology 1998; 28:555-561.
8. Traggiai E, Becker S, Subbarao K, et al. An efficient method to make human monoclonal antibodies from memory B cells: potent neutralization of SARS coronavirus. Nat Med. 2004; 10:871-5.
9. Cerino A, Mondelli M U. Identification of an immunodominant B-cell epitope on the hepatitis C virus non structural region defined by human monoclonal antibodies. J Immunol 1991; 147:2692-6.
10. Cerino A, Boender P, Rosa C, La Monica N, Habets W, Mondelli M U. A human monoclonal antibody specific for the N-terminus of hepatitis C virus nucleocapsid protein. J Immunol 1993; 151:7005-15.
11. Mondelli M U, Cerino A, Boender P, Oudshoorn P, Middeldorp J, Fipaldini C, La Monica N, Habets W. Significance of the immune response to a major, conformational B cell epitope on the hepatitis C virus NS3 region defined by a human monoclonal antibody. J Virol 1994; 68:4829-36.
12. Mondelli M U, Cerino A. Production of anti-HCV by human B cell clones and their characterization. In: Lau J Y N, Ed., "Hepatitis C Protocols", Methods in Molecular Medicine, The Humana Press Inc., Totowa U.S.A., 1998, p. 451-61.
13. Glebe D, Aliakbari M, Krass P, Knoop E V, Valerius K P, Gerlich W H. Pre-S1 Antigen-dependent infection of Tupaia hepatocyte cultures with human hepatitis B virus. J Virol 2003; 77:9511-21.
14. Ueda K, Tsurimoto T, Matsubara K. Three envelope proteins of hepatitis B virus: large S, middle S, and major S proteins needed for the formation of Dane particles. J Virol. 1991; 65: 3521-3529.
15. Barker, L. F., D. Lorenz, S. C. Rastogi, J. S. Finlayson, and E. B. Seligmann. 1977. Study of a proposed international reference preparation for antihepatitis B immunoglobulin. WHO Expert Committee on Biological Standardization technical report series. WHO Expert Committee on Biological Standardisation 29th Report BS 77.1164. Geneva, Switzerland, World Health Organization, 1977.
16. World Health Organization: Anti-hepatitis B immunoglobulin. WHO Tech Rep Ser 1978; 626:18.
17. Ferguson, M., M. W. Yu, A. Heath. Calibration of the second International Standard for hepatitis B immunoglobulin in an international collaborative study. Vox Sang 2010; 99:77-84.

18. Mast, E. E., C. M. Weinbaum, A. E. Fiore, M. J. Alter, B. P. Bell, L. Finelli, L. E. Rodewald, J. M. Douglas, Jr., R. S. Janssen, and J. W. Ward. 2006. A comprehensive immunization strategy to eliminate transmission of hepatitis B virus infection in the United States: recommendations of the Advisory Committee on Immunization Practices (ACIP) Part II: immunization of adults. MMWR Recomm. Rep. 55(RR-16):1-33.

The invention claimed is:

1. An antibody or fragment thereof capable of specifically binding to the Hepatitis B surface antigen (HBsAg) and having Hepatitis B Virus (HBV) neutralizing activity, wherein said antibody or fragment thereof comprises a light chain CDR1 region comprising the amino acid sequence of SEQ ID NO: 5, a light chain CDR2 region comprising the amino acid sequence of SEQ ID NO: 6, a light chain CDR3 region comprising the amino acid sequence of SEQ ID NO: 7, a heavy chain CDR1 region comprising the amino acid sequence of SEQ ID NO: 8, a heavy chain CDR2 region comprising the amino acid sequence of SEQ ID NO: 9 and a heavy chain CDR3 region comprising the amino acid sequence of SEQ ID NO: 10.

2. The antibody or fragment thereof according to claim 1, comprising both heavy ($V_H$) and light chain ($V_L$) variable domains wherein the $V_H$ domain comprises an amino acid sequence according to SEQ ID NO: 2 and wherein the $V_L$ domain comprises an amino acid sequence according to SEQ ID NO: 4.

3. The antibody or fragment thereof to claim 1, which is a human antibody.

4. The antibody or fragment thereof according to claim 1, wherein the antibody is a recombinant antibody.

5. A composition comprising the antibody or fragment thereof of claim 1.

6. A method for preventing or treating HBV infection or a disease caused thereby in a mammal, comprising administering to the mammal the antibody or fragment thereof of claim 1.

7. The method according to claim 6, wherein the antibody or fragment thereof is a human antibody or fragment thereof.

8. The method according to claim 6, wherein the antibody or fragment thereof comprises both heavy ($V_H$) and light chain ($V_L$) variable domains wherein the $V_H$ domain comprises an amino acid sequence according to SEQ ID NO: 2 and wherein the $V_L$ domain comprises an amino acid sequence according to SEQ ID NO: 4.

9. A nucleic acid encoding a heavy chain variable domain comprising the amino acid sequence of SEQ ID NO: 2 and a light chain variable domain comprising the amino acid sequence of SEQ ID NO: 4.

10. The nucleic acid according to claim 9, comprising the nucleotide sequence of SEQ ID NO: 1 and the nucleotide sequence of SEQ ID NO: 3.

11. A method of producing a recombinant antibody, comprising expressing the nucleic acid of claim 9, and recovering the antibody.

12. The method of claim 6, wherein the antibody or fragment thereof is administered to the mammal in an amount sufficient to maintain a minimum titer level of 12 IU/ml serum.

13. The method of claim 12, wherein the antibody or fragment thereof is administered to the mammal in an amount sufficient to maintain a titer level between about 100 and 500 IU/ml serum.

* * * * *

SEQUENCE LISTING

<160> NUMBER OF SEQ ID NOS: 10

<210> SEQ ID NO 1
<211> LENGTH: 369
<212> TYPE: DNA
<213> ORGANISM: homo sapiens

<400> SEQUENCE: 1

```
gaggtgcagg tgttggagtc tgggggaggc ttggtacagc cggggggtc cctgagactc      60
tcctgtgcag cctctggatt caggtttagc agctatgcca tgagttgggt ccgccaggct    120
ccagggaagg ggctggagtg ggtctcaggt attagtggta ctggtgaaaa cacatactac    180
gcagactccg tgaagggccg gttcaccatc tccagagaca attccaagaa cacgctgtac    240
gtgcaaatga acagcctgag agccgaagac acggccgtat attactgtgc gaaagatgcg    300
atcttgggca gtggccaccc ctggtacttc catgtctggg gccgtggcac cctggtcact    360
gtctcctca                                                             369
```

<210> SEQ ID NO 2
<211> LENGTH: 123
<212> TYPE: PRT
<213> ORGANISM: homo sapiens

<400> SEQUENCE: 2

```
Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Arg Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Gly Thr Gly Glu Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Asn Ser Leu Arg Ala Glu Asp Thr Ala Val Tyr Tyr Cys
                85                  90                  95

Ala Lys Asp Ala Ile Leu Gly Ser Gly His Pro Trp Tyr Phe His Val
            100                 105                 110

Trp Gly Arg Gly Thr Leu Val Thr Val Ser Ser
        115                 120
```

<210> SEQ ID NO 3
<211> LENGTH: 324
<212> TYPE: DNA
<213> ORGANISM: homo sapiens

<400> SEQUENCE: 3

```
tcctatgtgc tgactcagcc tccctcggtg tcagtggccc caggacagac ggccaggatg      60
acctgtgggg gaaacaacat tggaagtgaa agtgtgcact ggttccagca gaagccaggc    120
caggcccctg tgctggtcgt ctatgatgat agcgaccggc cctcagggat ccctgagcga    180
ttctctggct ccaactctgg gaacacggcc accctgacca tcagtagggt cgaagccggg    240
gatgaggccg actattactg tcaggtgtgg gatagtagta gtgatcatgc tgtgttcgga    300
```

```
ggaggcaccc agctgaccgt cctc                                              324
```

<210> SEQ ID NO 4
<211> LENGTH: 108
<212> TYPE: PRT
<213> ORGANISM: homo sapiens

<400> SEQUENCE: 4

Ser Tyr Val Leu Thr Gln Pro Pro Ser Val Ser Val Ala Pro Gly Gln
1               5                   10                  15

Thr Ala Arg Met Thr Cys Gly Gly Asn Asn Ile Gly Ser Glu Ser Val
            20                  25                  30

His Trp Phe Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Ala Val Phe Gly Gly Gly Thr Gln Leu Thr Val Leu
            100                 105

<210> SEQ ID NO 5
<211> LENGTH: 6
<212> TYPE: PRT
<213> ORGANISM: homo sapiens

<400> SEQUENCE: 5

Asn Ile Gly Ser Glu Ser
1               5

<210> SEQ ID NO 6
<211> LENGTH: 3
<212> TYPE: PRT
<213> ORGANISM: homo sapiens

<400> SEQUENCE: 6

Asp Asp Ser
1

<210> SEQ ID NO 7
<211> LENGTH: 9
<212> TYPE: PRT
<213> ORGANISM: homo sapiens

<400> SEQUENCE: 7

Gln Val Trp Asp Ser Ser Asp His
1               5

<210> SEQ ID NO 8
<211> LENGTH: 9
<212> TYPE: PRT
<213> ORGANISM: homo sapiens

<400> SEQUENCE: 8

Gly Phe Arg Phe Ser Ser Tyr Ala Met
1               5

<210> SEQ ID NO 9
<211> LENGTH: 8

```
<212> TYPE: PRT
<213> ORGANISM: homo sapiens

<400> SEQUENCE: 9

Ile Ser Gly Thr Gly Glu Asn Thr
1               5

<210> SEQ ID NO 10
<211> LENGTH: 16
<212> TYPE: PRT
<213> ORGANISM: homo sapiens

<400> SEQUENCE: 10

Ala Lys Asp Ala Ile Leu Gly Ser Gly His Pro Trp Tyr Phe His Val
1               5                   10                  15
```